(12) United States Patent
Luppi

(10) Patent No.: US 6,792,623 B2
(45) Date of Patent: Sep. 21, 2004

(54) HELMET FOR ARTIFICIAL RESPIRATION WITHOUT THE AID OF MASKS

(75) Inventor: Libero Luppi, Mirandola (IT)

(73) Assignee: Starmed S.p.A., Mirandola (IT)

( * ) Notice: Subject to any disclaimer, the term of this patent is extended or adjusted under 35 U.S.C. 154(b) by 0 days.

(21) Appl. No.: 10/316,928

(22) Filed: Dec. 12, 2002

(65) Prior Publication Data

US 2003/0135915 A1 Jul. 24, 2003

(30) Foreign Application Priority Data

Jan. 24, 2002 (IT) .......................................... MI20020121

(51) Int. Cl.[7] .............................. A42C 5/04; A42B 1/08; A62B 29/00
(52) U.S. Cl. ................................ 2/171.3; 2/413; 2/424; 128/200.28; 128/201.23; 128/201.24; 128/205.26
(58) Field of Search ......................... 2/171.3, 424, 413, 2/205; 128/205.26, 200.28, 201.24, 201.23

(56) References Cited

U.S. PATENT DOCUMENTS

| | | | | |
|---|---|---|---|---|
| 2,240,751 A | * | 5/1941 | Boesger | 128/201.23 |
| 2,418,473 A | * | 4/1947 | Lambertsen | 128/205.26 |
| 2,742,900 A |   | 4/1956 | Giorgio et al. | |
| 2,850,011 A | * | 9/1958 | Schaefer | 128/201.28 |
| 2,888,011 A |   | 5/1959 | Clark et al. | |
| 3,042,926 A | * | 7/1962 | Shepard | 2/2.14 |
| 3,438,060 A | * | 4/1969 | Gregory et al. | 2/6.3 |
| 3,786,809 A |   | 1/1974 | Kitrilakis | |
| 3,889,670 A | * | 6/1975 | Loveland et al. | 128/203.12 |
| 4,022,200 A |   | 5/1977 | Jonson | |
| 4,215,437 A | * | 8/1980 | Kao | 2/424 |
| 4,236,514 A | * | 12/1980 | Moretti | 128/201.23 |
| 4,458,680 A | * | 7/1984 | Childers et al. | 128/201.29 |
| 4,605,000 A | * | 8/1986 | Anguita | 128/201.25 |
| 4,620,538 A |   | 11/1986 | Koegek et al. | |
| 4,683,880 A | * | 8/1987 | Werjefelt | 128/201.28 |
| 4,763,664 A | * | 8/1988 | Merilainen | 600/531 |
| 5,104,430 A | * | 4/1992 | Her-Mou | 55/385.1 |
| 5,566,668 A | * | 10/1996 | Jesadanont | 128/201.26 |
| 5,890,232 A | * | 4/1999 | Park | 2/413 |
| 6,321,764 B1 | * | 11/2001 | Gauger et al. | 135/128 |

FOREIGN PATENT DOCUMENTS

| | | |
|---|---|---|
| EP | 1 170 026 | 1/2002 |
| GB | 828 731 | 2/1960 |

* cited by examiner

Primary Examiner—Rodney M. Lindsey
(74) Attorney, Agent, or Firm—Guido Modiano; Albert Josif; Daniel O'Byrne

(57) ABSTRACT

A helmet for artificial respiration without the aid of masks, comprising a containment body with at least one optically transparent portion, which can accommodate hermetically the head of a patient. The containment body has an air intake port that can be connected to a ventilation apparatus and an outlet port. The helmet further comprises, on the containment body, substantially at the mouth of the patient being treated, an opening that can be closed removably by a closure element.

16 Claims, 4 Drawing Sheets

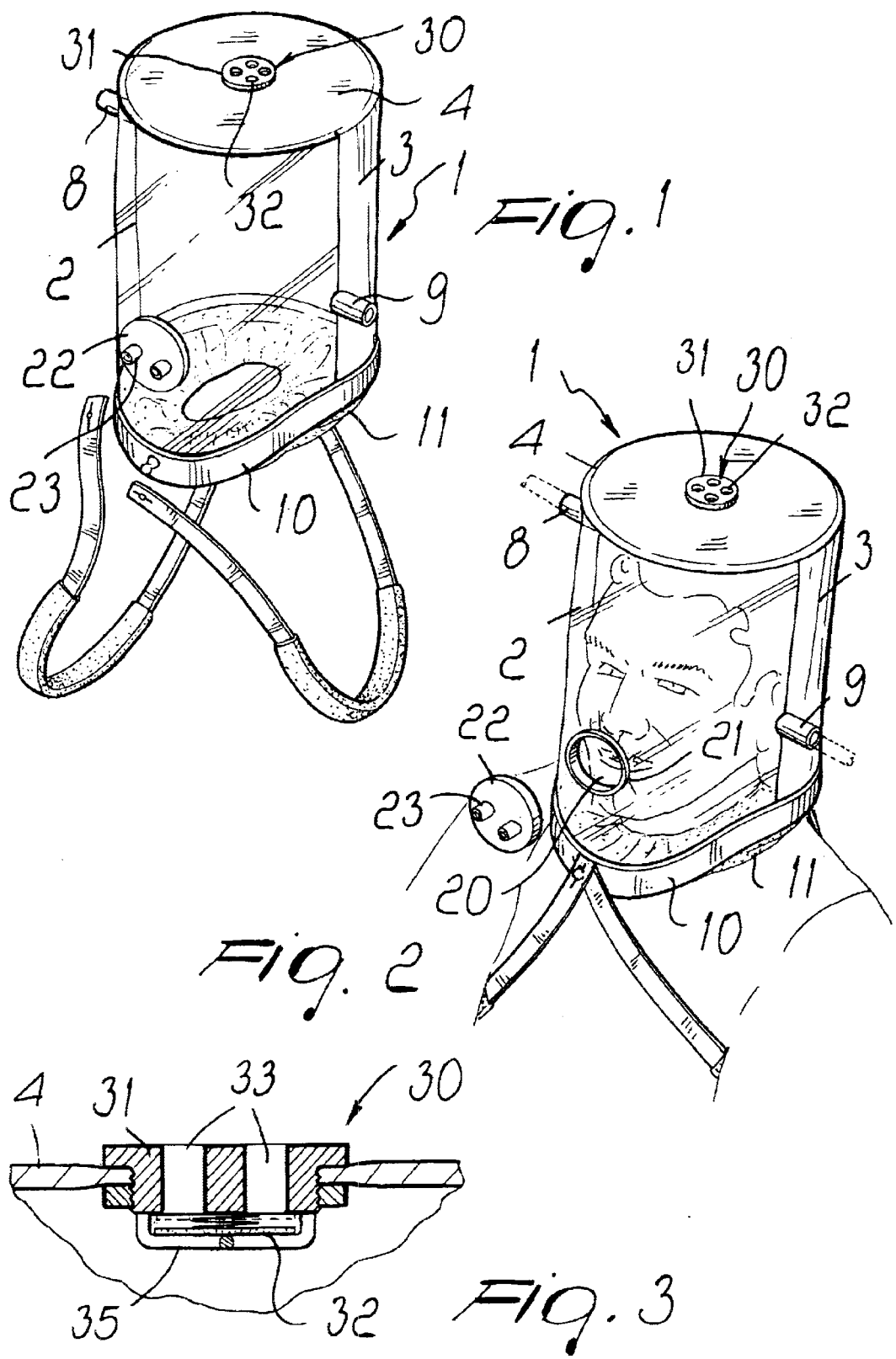

US 6,792,623 B2

HELMET FOR ARTIFICIAL RESPIRATION WITHOUT THE AID OF MASKS

BACKGROUND OF THE INVENTION

The present invention relates to improvements to helmets for artificial respiration without the aid of masks.

EPA 01113685.0 by this same Applicant, assumed included herein by reference, discloses a helmet for artificial respiration without the aid of masks that has proved to be valid in many respects, since it allows to achieve a high degree of safety by way of the presence of an antisuffocation valve and because straps are provided to produce a firm coupling of the helmet to the patient, avoiding the unpleasant phenomenon of lifting during use.

SUMMARY OF THE INVENTION

This helmet has been found to be susceptible of improvements, and the aim of the present invention is indeed to provide a helmet that allows to increase its versatility and to offer the possibility to reduce to a minimum the internal volume of the helmet, thus reducing dead spaces.

Within this aim, an object of the present invention is to provide a helmet that if necessary allows to rapidly act on the patient without having to remove said helmet.

Another object of the invention relates to the possibility to optimize the antisuffocation valve, thus allowing to increase the safety characteristics considerably.

Another object of the present invention is to provide a helmet that while having considerably improved characteristics still has a simplified structure and a competitive cost.

This aim and these and other objects that will become better apparent hereinafter are achieved by a helmet for artificial respiration without the aid of masks, according to the invention, comprising a containment body with at least one optically transparent portion, which can accommodate hermetically the head of a patient, said containment body having an air intake port that can be connected to a ventilation apparatus and an outlet port, characterized in that it comprises, on said containment body, substantially at the mouth of the patient being treated, an opening that can be closed removably by a closure element.

BRIEF DESCRIPTION OF THE DRAWINGS

Further characteristics and advantages of the invention will become better apparent from the following detailed description of a preferred but not exclusive embodiment of a helmet for artificial respiration without the aid of masks, illustrated only by way of non-limitative example in the accompanying drawings, wherein:

FIG. 1 is a schematic perspective view of the helmet according to the invention;

FIG. 2 is a perspective view of the helmet while worn;

FIG. 3 is a sectional view of a possible embodiment of the antisuffocation valve of the helmet according to the invention;

DESCRIPTION OF THE PREFERRED EMBODIMENTS

Figure 4:
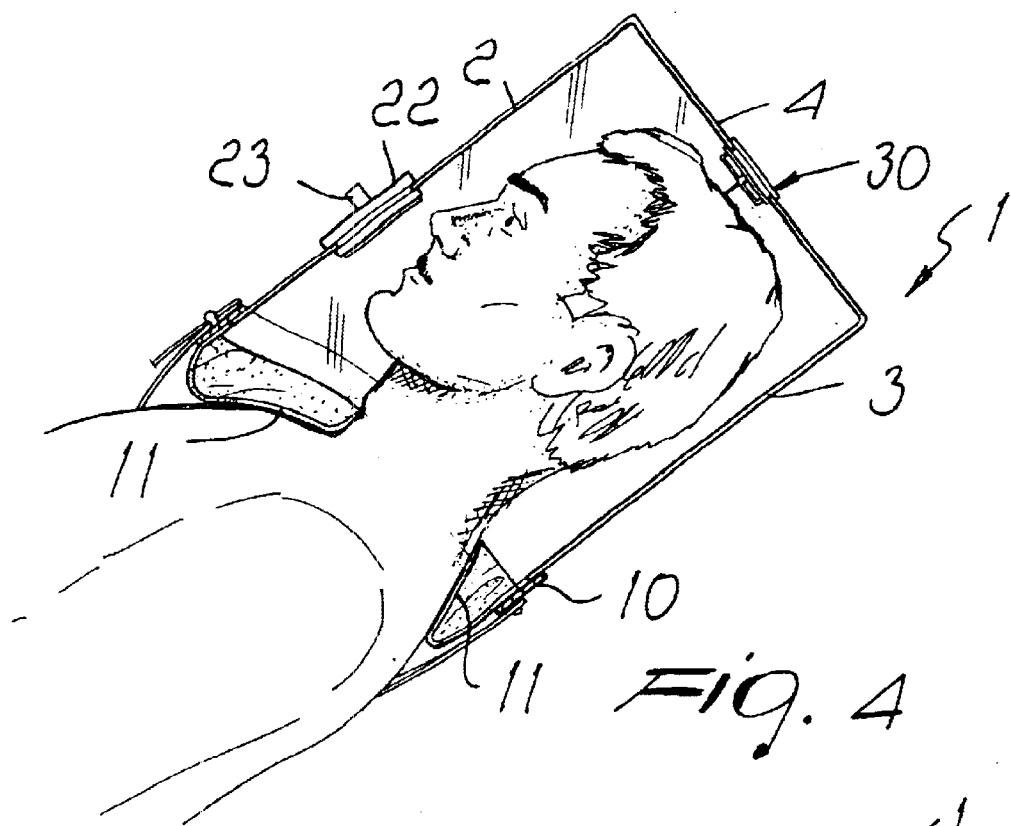
FIG. 4 is a sectional view of the helmet while worn.
Figure 5:
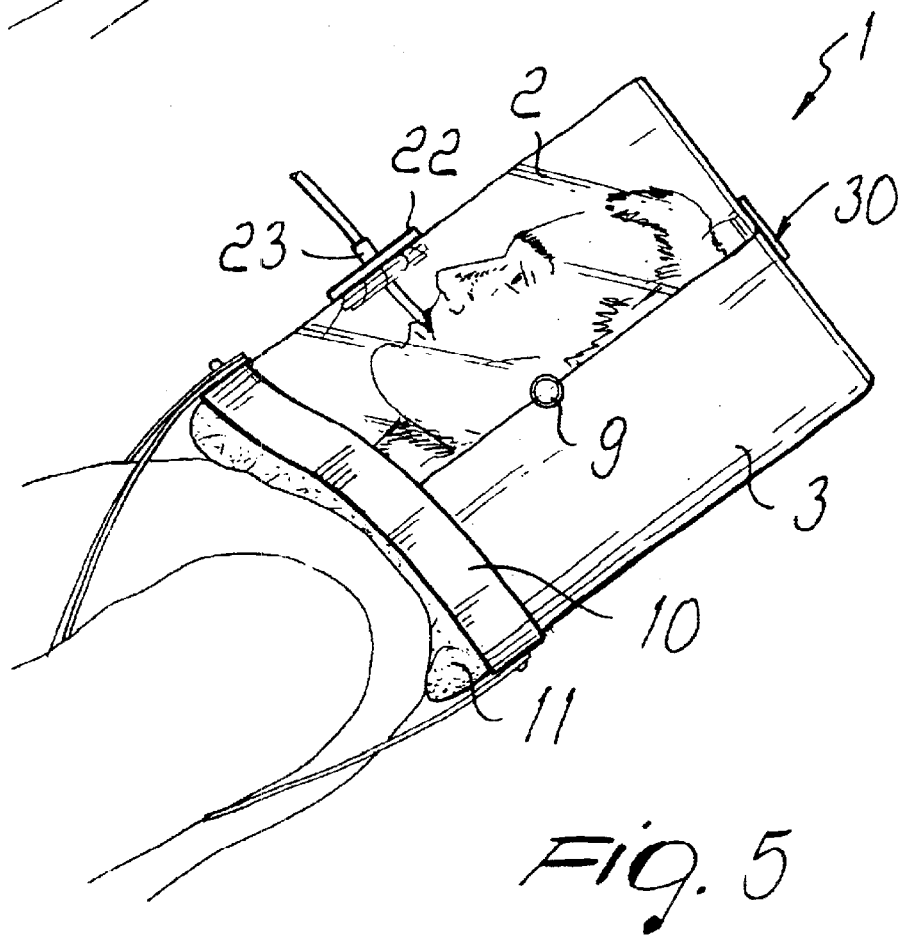
FIG. 5 is a sectional view of the helmet during its use, with the application of tubes and/or catheters to the patient.

With reference to the figures, the helmet for artificial respiration without the aid of masks, according to the invention, comprises a containment body, generally designated by the reference numeral 1, which is constituted by a front portion 2 made of optically transparent semirigid material that is preferably non-deformable and is connected to a rear portion 3 that is not transparent. The side wall formed by the front portion 2 and by the rear portion 3 is closed by a top element 4.

A base ring 10 is provided at the open end and is advantageously anatomically contoured and is in practice folded downward in its front portion and optionally also in its rear part in order to assume a saddle-like configuration, so that it is arranged proximate to the body of the patient in the region that forms the joining edge of a deformable sealing collar 11.

With this arrangement, the deformable collar 11 finds a smaller dead space into which it can expand during the respiratory work of the patient with the aid of ventilation machines.

This solution, together with the correct shaping of the containment body, allows to minimize the dead spaces into which the deformable collar 11 can expand during respiratory work; this allows greater reactivity in reading the negative pressure during the inspiration step of respiration.

Another important aspect of the invention is constituted by the fact that an opening 20 is provided substantially at the mouth of the patient being treated and is formed by a connection port 21 connected to the optically transparent portion; such opening can be closed hermetically by a closure element, which can be constituted by a closure plug 22 that is connected with a screw or bayonet coupling or by means of other suitable systems such as gate valves or closure flaps.

Advantageously, the closure plug has one or more ports 23, which allow to insert hermetically nasogastric tubes, feeding cannulas and the like, since these elements can be inserted hermetically in the ports provided in the closure plug or in the optional similar element that closes the opening 20.

Another aspect that characterizes the invention relates to a particular structure of the antisuffocation valve, generally designated by the reference numeral 30, which can be applied directly to the closure plug or optionally in another portion of the surface of the containment body, such as for example the top.

The antisuffocation valve 30 has a flat body 31, which forms a plurality of through holes 32 that lead outward and are affected, inside the containment body 1, by a floating membrane or disk 33, which is accommodated within a cage or crosspiece 35 that allows to keep the floating disk 33 proximate to the holes.

With this arrangement of the valve, during the normal operation of the helmet air is introduced through an air intake port 8, which can be connected to the ventilation apparatus, and exits through an outlet port 9, which is also provided on the containment body; the pressure generated inside the helmet causes the floating disk to produce an optimum seal since the floating disk itself acts against the flat body, in practice closing the holes.

An accidental drop in air flow and/or pressure allows the immediate opening of the valve by way of the fact that the floating disk, due to its own weight and/or to the action of a preadjusted spring, frees the holes 32, allowing the free circulation of air and of the respiratory flow, both during inspiration and during expiration, thus achieving a solution that is particularly valid and safe. Moreover, when the flow and/or pressure are restored, the floating disk 33 must be repositioned manually against the holes 32 so as to close them and remains thereat during therapy.

Figure 7:
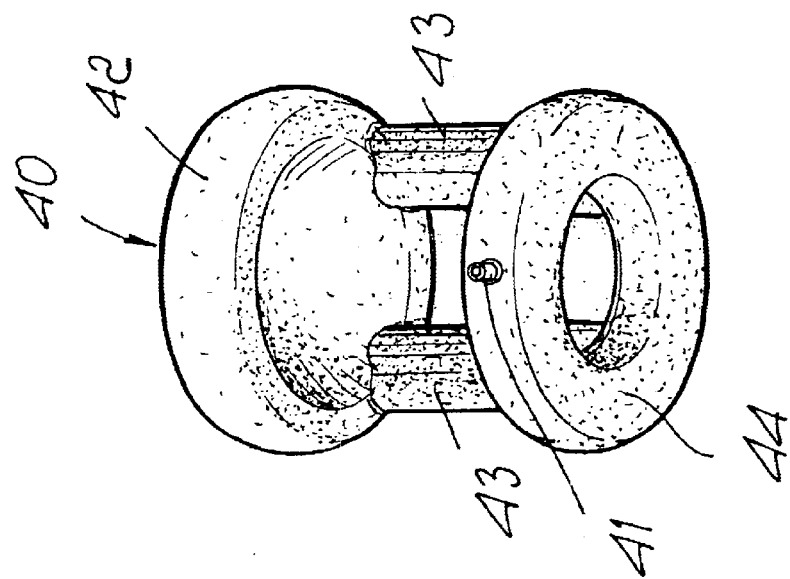
FIG. 7 is a schematic perspective view of the means for reducing dead space.
Figure 6:
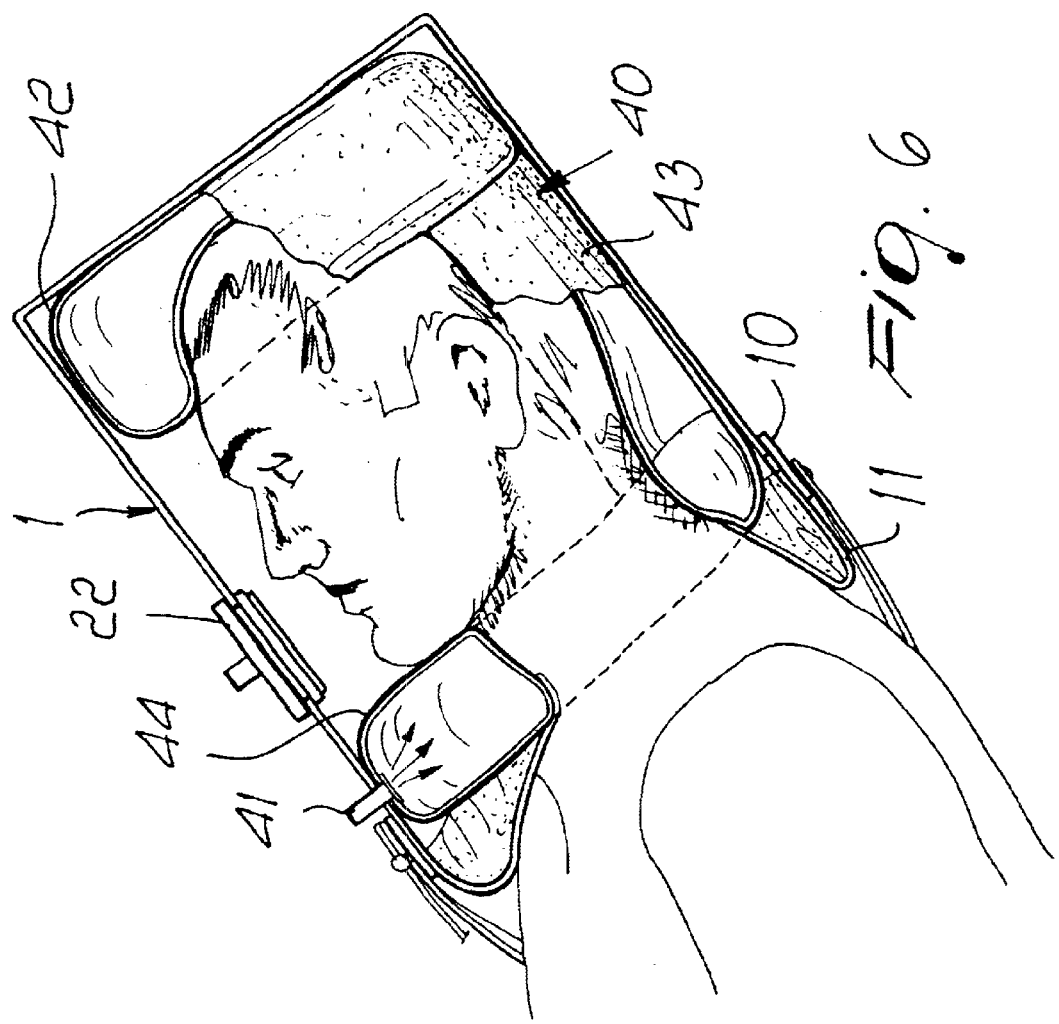
FIG. 6 is a sectional view of a helmet with means for reducing dead space.

FIGS. 6 and 7 illustrate a helmet in which the internal dead space is reduced significantly, thus achieving the advantages that are typical of conventional masks without the drawbacks of limited comfort that are typical of masks.

In the specific case, means to reduce the dead space are provided inside the containment body 1 and are constituted by a bag 40, which can be integrated directly in the containment body or can be a separate element and can be inflated by means of a duct 41 that can be accessed from the outside of the containment body 1.

Advantageously, the bag 40 has an upper dome 42, which affects the upper part of the head and is connected, by means of lateral bodies 43 located at the sides of the head, to a collar-like part 44 that is arranged at the neck of the patient.

This arrangement minimizes dead space, with a consequent better reactivity of the system which, in assisted ventilation, allows the ventilator to detect promptly the pressure drop at the beginning of inspiration, activating immediately the ventilator for delivery.

Figure 8:
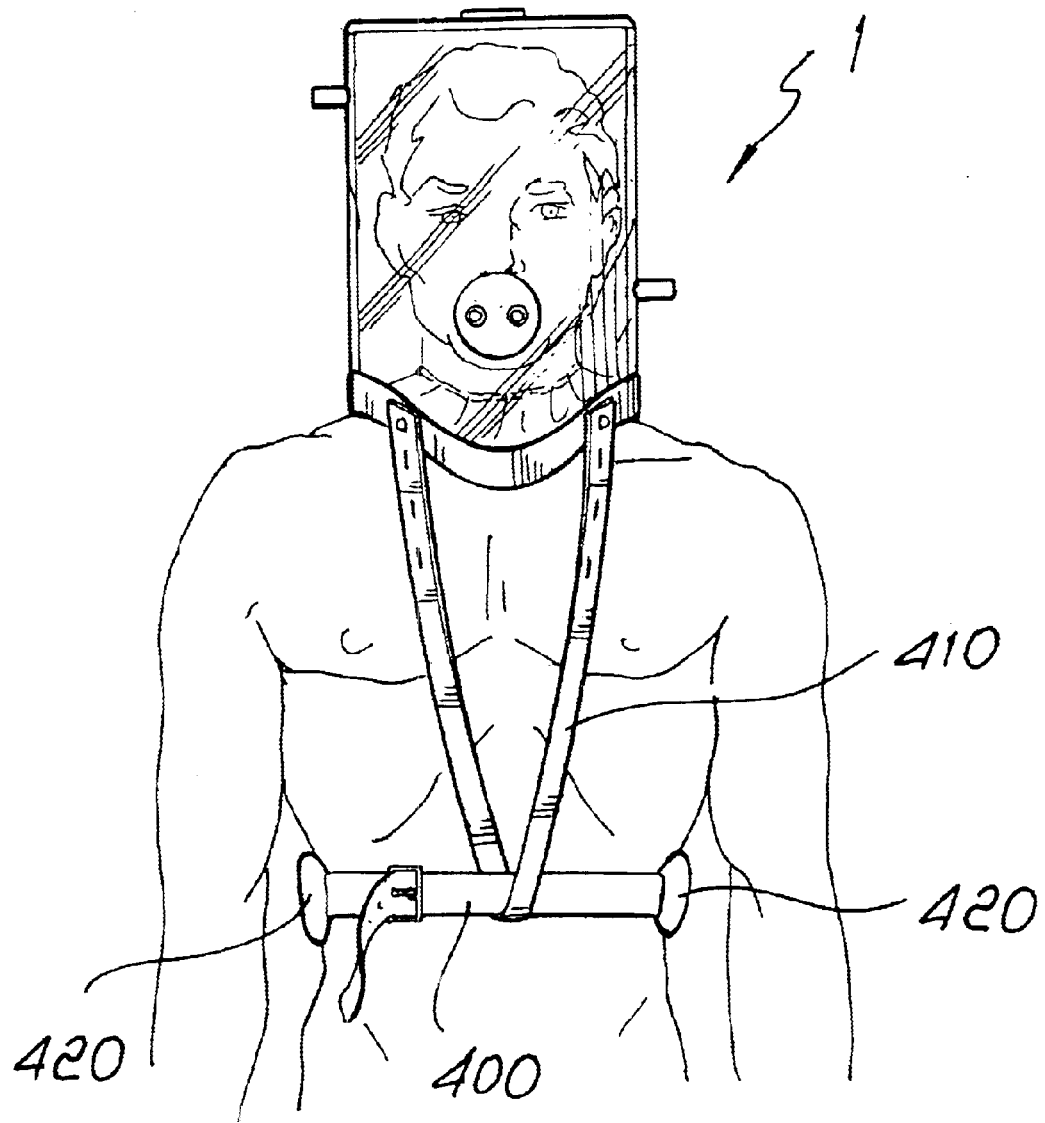
FIG. 8 is a view of a helmet with different means for connection to the patient.

With reference to FIG. 8, different means for connection to the patient are illustrated which allow to avoid the pressure of the straps on the armpits, which in the long term might cause pain that is not always tolerable for patients.

This embodiment provides for a band or belt 400, which can be arranged circumferentially around the chest, with pads 420 optionally interposed; connection straps 410, arranged preferably at the front and rear of the containment body, are coupled to the belt 400.

The belt ensures a wide contact surface, which reduces the specific load and allows to discharge the upward thrust applied by the straps.

This operation is very advantageous, since it allows a less traumatic use of the device and also provides an alternative to the underarm use of straps.

From the above description it is thus evident that the invention achieves the intended aim and objects, and in particular the fact is stressed that a helmet for artificial respiration is provided which is particularly valid and functional, allowing to reduce dead spaces inside the helmet, to freely access the mouth of the patient without having to remove the helmet, and to also have a very high degree of safety.

The invention thus conceived is susceptible of numerous modifications and variations, all of which are within the scope of the inventive concept.

All the details may further be replaced with other technically equivalent elements.

In practice, the materials employed, so long as they are compatible with the specific use, as well as the contingent shapes and dimensions, may be any according to requirements.

The disclosures in Italian Patent Application No. MI2002A000121 from which this application claims priority are incorporated herein by reference.

What is claimed is:

1. A helmet for artificial respiration without the aid of masks, comprising a containment body with at least one optically transparent portion, which can accommodate hermetically the head of a patient, said containment body having an air intake port that can be connected to a ventilation apparatus and an outlet port such that in normal operation of the helmet an air flow pressure is produced inside the helmet from air introduced into said intake port and air exiting from said outlet port, an antisuffocation valve being connected to said containment body, wherein said antisuffocation valve comprises a flat body that forms a plurality of through holes or slots that lead outside and are affected, inside said containment body, by a floating disk or membrane that is held in position by a cage or crosspiece and that acts against said flat body and closes and seals said through holes during said normal operation of the helmet, and furthermore said floating disk is suitable to disengage from said holes for a pressure value, inside said helmet, that is lower than a preset value.

2. The helmet according to claim 1, further comprising, on said containment body, substantially at the mouth of the patient being treated, an opening that can be closed removably by a closure element.

3. The helmet according to claim 2, comprising a port that is connected to said optically transparent portion and forms said opening.

4. The helmet according to claim 2, wherein said closure element is constituted by a closure plug.

5. The helmet according to claim 2, comprising, on said closure element, at least one port for inserting hermetically tubes.

6. The helmet according to claim 1, said containment body having a base ring to which the lateral surface of said helmet is connected, wherein said base ring is shaped so as to be arranged proximate to the body of the patient at a joining edge of a deformable sealing collar.

7. The helmet according to claim 6, wherein said base ring has a portion that is folded downward in a front region.

8. The helmet according to claim 6, wherein said base ring has a portion that is folded downward in a rear region.

9. The helmet according to claim 1, wherein said antisuffocation valve is provided on the top of said containment body.

10. The helmet according to claim 1, further comprising, inside said containment body, means for reducing dead space.

11. The helmet according to claim 10, wherein said means for reducing dead space comprise an inflatable bag.

12. The helmet according to claim 11, wherein said inflatable bag is integrated directly in said containment body.

13. The helmet according to claim 11, wherein said inflatable bag is an element that can be separated from said containment body.

14. The helmet according to claim 11, comprising a duct that can be accessed from the outside of said containment body and is connected to said inflatable bag.

15. The helmet according to claim 11, wherein said inflatable bag comprises an upper dome that affects the upper part of the head and is connected, by means of lateral bodies that can be arranged laterally to the head, to a collar-like portion that can be arranged at the neck of the patient.

16. The helmet according to claim 1, further comprising means for connection to the patient which are constituted by a band or belt that can be arranged circumferentially with respect to the chest and with which at least one connection strap associable with said containment body is coupled.

* * * * *